(12) United States Patent
Shiramizu et al.

(10) Patent No.: US 10,018,557 B2
(45) Date of Patent: Jul. 10, 2018

(54) TERAHERTZ WAVE MEASURING DEVICE

(71) Applicant: HITACHI HIGH-TECHNOLOGIES CORPORATION, Tokyo (JP)

(72) Inventors: Nobuhiro Shiramizu, Tokyo (JP); Hideharu Mikami, Toyko (JP); Koichi Watanabe, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/553,176

(22) PCT Filed: Mar. 13, 2015

(86) PCT No.: PCT/JP2015/057487
§ 371 (c)(1),
(2) Date: Aug. 24, 2017

(87) PCT Pub. No.: WO2016/147253
PCT Pub. Date: Sep. 22, 2016

(65) Prior Publication Data
US 2018/0080868 A1    Mar. 22, 2018

(51) Int. Cl.
*G01N 21/3581* (2014.01)

(52) U.S. Cl.
CPC ... *G01N 21/3581* (2013.01); *G01N 2201/061* (2013.01)

(58) Field of Classification Search
CPC ............... G01N 21/3581; G01N 2201/061
See application file for complete search history.

(56) References Cited

U.S. PATENT DOCUMENTS

| 7,750,276 B2 | 7/2010 | Miyamoto et al. |
| 2002/0024718 A1 | 2/2002 | Kawase et al. |
| 2015/0036472 A1 | 2/2015 | Saito et al. |

FOREIGN PATENT DOCUMENTS

| JP | 2002-72269 | 3/2002 |
| JP | 2014-16303 | 1/2014 |
| JP | 2014-81345 | 5/2014 |

(Continued)

OTHER PUBLICATIONS

International Search Report for PCT/JP2015/057487 dated Jun. 2, 2015.

(Continued)

*Primary Examiner* — Mark R Gaworecki
(74) *Attorney, Agent, or Firm* — Mattingly & Malur, PC

(57) ABSTRACT

The terahertz wave measuring device includes a pulsed laser light generation unit 1, a seed light generation unit 2, a terahertz wave generator 5 that generates terahertz waves, a terahertz wave detector 8 on which the terahertz waves that are generated from the terahertz wave generator and that have interacted with a measurement object 7 and the pump light are incident and that generates terahertz wave detection light 9, an interference optical system 11 that multiplexes the terahertz wave detection light and reference light 14 of the same wavelength as the terahertz wave detection light to generate a plurality of interfering light beams 12, a plurality of light detectors 13 that detect the interfering light beams, and a signal processing unit 16 that outputs an intensity signal and/or a phase signal of the terahertz waves by performing arithmetic operations on the outputs of the plurality of light detectors.

11 Claims, 13 Drawing Sheets

(56) References Cited

FOREIGN PATENT DOCUMENTS

JP        2015-28823        2/2015

OTHER PUBLICATIONS

Shinichiro Hayashi, et al., "Terahertz-wave Parametric Generation and Detection System Covering the Range From 1 to 3 THz" in 2013 Conference on Lasers and Electro-Optics Pacific Rim, (Optical Society of America, 2013), paper WPC_15.

Shinichiro Hayashi, et al., "Coherent Monochromatic Terahertz-wave Pulse Detection using Nonlinear Parametric Conversion at Room Temperature", in CLEO: 2014, OSA Technical Digest (online) (Optical Society of America, 2014), paper JTh2A.62.

TERAHERTZ WAVE MEASURING DEVICE

TECHNICAL FIELD

The present invention relates to a terahertz wave measuring apparatus.

BACKGROUND ART

A terahertz wave measuring apparatus is an apparatus that irradiates a measured object with a terahertz wave and observes a reflected wave or a transmitted wave to detect an intensity change or a phase difference generated by the measured object. A terahertz wave measuring apparatus is an apparatus that is effective for non-destructively observing components contained in the measured object.

The terahertz wave is an electromagnetic wave in a frequency range of substantially 0.1 THz to 10 THz and has features superior in transmissibility to many substances such as paper, wood, and plastic compared with a far infrared ray that is the electromagnetic wave of a higher frequency band, and superior in rectilinearity and resolution compared with a millimeter wave that is an electromagnetic wave of a lower frequency band.

In addition, an intrinsic spectrum of many substances including polymer compounds such as sugars and proteins is included in the frequency band of the terahertz wave. It is possible to non-destructively observe a shape and an internal structure of the measured object, presence/absence of defects/foreign matters, a difference in material and contained component, and the like while being in a transparent container by taking advantage of these features, by irradiating the measured object with the terahertz wave, and by observing the transmitted wave or the reflected wave. In addition, it is possible to non-destructively observe surface irregularities of the measured object, a thickness of a layer in a layer structure, and an internal structure such as a hollow by detecting a difference in phase between a terahertz wave reflected on the measured object and a terahertz wave reflected on a reference metal. Therefore, it is expected that a wide range of terahertz wave application technologies applicable to pharmaceutical inspection, material inspection, and structural inspection will be realized in the future.

However, since the terahertz wave technology of the related art is difficult to achieve both a highly output terahertz wave generator and highly sensitive terahertz wave detector, and it is difficult to be downsized, the spread of terahertz wave technology is not progressed for industrial applications such as a product inspection apparatus. Therefore, research and development of technologies that can achieve downsizing, high output and high sensitivity are promoted.

As a terahertz wave measuring system recently developed in order to achieve the high output and high sensitivity of the terahertz wave, for example, an injection-seeded Terahertz-wave Parametric Generator (is-TPG) disclosed in NPL 1 is known. This technique includes a method for generating the terahertz wave having high intensity by improving a method for generating a terahertz wave described in PTL 2 and a detecting method with high sensitivity using a nonlinear optical crystal.

A feature of this technique is that the nonlinear optical crystal is used both for the terahertz wave for generation and the terahertz wave for detection. When the nonlinear optical crystal for generation is irradiated with a pump beam and a seed beam having two wavelengths at an appropriate angle, a narrow-band terahertz wave is generated as a difference frequency component. In addition, when the nonlinear optical crystal for detection is irradiated with the pump beam and the terahertz wave at an appropriate angle, the infrared light having the same wavelength as that of the seed beam is outputted as a detection light. It is possible to utilize various infrared sensors that are highly sensitive to the observation of a detection light, to observe the terahertz wave which is weaker than that of a system of the related art using a silicon bolometer or pyrometer that directly observes the terahertz wave, and to obtain a high SN ratio of substantially 100 dB with respect to the intensity.

In addition, as illustrated in NPL 2, a method for detecting a phase with respect to an optical path length of the terahertz wave is known, in which the method is performed by observing a change in the intensity of the detection light while causing the optical path length of the terahertz wave to transit by causing an idler beam along with the pump beam be incident on the nonlinear optical crystal on which the terahertz wave is incident.

On the other hand, a homodyne phase diversity detection system disclosed in PTL 1 is known as means for detecting a minute optical signal with high sensitivity in the field of information reproduction recorded on an optical disk although not in the field of measurement.

CITATION LIST

Patent Literature

PTL 1: U.S. Pat. No. 7,750,276 B2
PTL 2: JP Patent Publication (Kokai) 2002-072269 A

Non-Patent Literature

NPL 1: Shinichiro Hayashi, et al., "Terahertz-wave Parametric Generation and Detection System Covering the Range From 1 to 3 THz" in 2013 Conference on Lasers and Electro-Optics Pacific Rim, (Optical Society of America, 2013), paper WPC_15.

NPL 2: Shinichiro Hayashi, et al., "Coherent Monochromatic Terahertz-wave Pulse Detection using Nonlinear Parametric Conversion at Room Temperature", in CLEO: 2014, OSA Technical Digest (online) (Optical Society of America, 2014), paper JTh2A.62.

SUMMARY OF INVENTION

Technical Problem

FIG. 17 is a schematic diagram illustrating a configuration of an is-TPG system which is a terahertz wave measuring apparatus of the related art. A pump beam 3 having high intensity is incident on a terahertz wave generator 5 configured of a nonlinear optical crystal from a pump beam generator 1 configured of a pulse laser; and a seed beam 4 is incident on the terahertz wave generator 5 from a seed beam generator 2 configured of a continuous wave variable wavelength laser. Normally, LiNbO$_3$ to which MgO is added is used for the nonlinear optical crystal. A measured object 7 is irradiated with a terahertz wave 6 generated from the terahertz wave generator 5 and the terahertz wave transmitting the measured object 7 is incident on a terahertz wave detector 8 together with the pump beam 3. Then, a terahertz wave detection beam 9 generated from the terahertz wave detector 8 is detected by a photodetector 812.

FIG. 18 is a schematic diagram illustrating configurations of a terahertz wave generator and a terahertz wave detector, and a direction of each light and the terahertz wave. Here, when a wave vector and a frequency of the pump beam are respectively $k_p$ and $f_p$, a wave vector and a frequency of the seed beam are respectively $k_i$ and $f_i$, a wave vector and the frequency of the generated terahertz wave 6 are respectively $k_T$ and $f_T$, Expressions (1) and (2) are referred to as a phase matching condition.

$$f_p = f_T + f_i \qquad (1)$$

$$k_p = k_T + k_i \qquad (2)$$

Since a refractive index of the nonlinear optical crystal varies depending on an infrared light and the terahertz wave, $k_p$, $k_i$, and $k_T$ are not parallel. In addition, an angle θ between the wave vectors $k_p$ and $k_i$ is referred to as a phase matching angle. The phase matching angle increases depending on the frequency $f_T$. When the seed beam 4 and the pump beam 3 are incident on a nonlinear optical crystal 21 of the terahertz wave generator 5 at the angle θ (substantially 2°) so as to satisfy the phase matching condition, the strong terahertz wave 6 is irradiated in a direction of $\theta_T$ (substantially 65°) by an optical parametric process. A silicon prism 22 is in close contact with the nonlinear optical crystal in order to avoid a total reflection of the terahertz wave at a nonlinear optical crystal interface and to take it out to an outside. Since the refractive indices of LiNbO$_3$ and silicon to the terahertz wave are respectively substantially 5.3 and substantially 3.4, the terahertz wave 6 is irradiated in a $\theta'_T$ direction (substantially 50°) according to Snell's law. A terahertz emitting surface of the silicon prism 22 is cut at substantially 40° with respect to an incident surface so that the terahertz wave passes through the terahertz emitting surface without being reflected substantially vertically.

When the terahertz wave 6 transmitted through or reflected by the measured object 7 is incident on the nonlinear optical crystal 21 via the silicon prism 22 of the terahertz wave detector 8 at the angle $\theta'_T$ formed with the pump beam 3, the terahertz wave detection beam 9 is generated in the direction of the angle θ by the optical parametric process with the pump beam. The terahertz wave detection beam is detected by the photodetector 812.

A problem of the is-TPG system is that weak terahertz wave detection beam is blocked by a background light generated from the terahertz wave detector by the incidence of the pump beam. As illustrated in FIG. 18, a weak background light 10 is irradiated from the terahertz wave detector 8 together with the terahertz wave detection beam 9. Unlike the terahertz wave detection beam 9, an irradiation direction of the background light 10 spreads in a range of substantially 1° to 3° without depending on the frequency of the terahertz wave. A frequency of the background light 10 also spreads in a measurement range around 2.2 THz. In addition, the background light is generated even in a case where the terahertz wave is not incident on the terahertz wave detector 8.

FIG. 19 is a graph illustrating an intensity difference between an intensity of the terahertz wave detection beam and an intensity of the background light measured using the is-TPG system of the related art. In a case where the terahertz wave detection beam does not block the terahertz wave, the background light indicates frequency dependence in a case of blocking the terahertz wave. When measuring the background light, although the terahertz wave is not incident, a signal that is maximized around 2.2 THz is generated. Therefore, when measuring the measured object having a low terahertz wave transmittance, the terahertz wave detection beam is weaker than the background light and is difficult to be detected despite the fact that the terahertz wave detection beam exceeds the minimum light reception sensitivity of a photodetector. It is possible to observe the weak terahertz wave detection beam by separating the background light and to improve a measurement dynamic range of the terahertz wave. However, since the background light and the terahertz wave detection beam are generated in substantially the same wavelength in the same direction, it is difficult to separate them by a bandpass filter. Therefore, a method for separating using a space filter configured by a pinhole or the like is disclosed in NPL 1. FIG. 17 illustrates a configuration of background light separation using the space filter. Since the background light 10 emitted from the terahertz wave detector 8 is generated in the range of substantially 1° to 3° regardless of the frequency of the terahertz wave, the terahertz wave detection beam 9 and the background light 10 are incident on a space filter 811 configured of a pinhole separated from the terahertz wave detector 8 by a distance of several meters. The terahertz wave detection beam which is not diffused by the distance transmits an aperture of the pinhole, and the diffused background light is almost blocked except for the aperture. It is possible to separate the weak terahertz wave detection beam from the background light by detecting the transmitted terahertz wave detection beam by the photodetector 812.

In this means, in order to diffuse the background light, an optical path length of usually several meters or more is required and the apparatus becomes large-sized. In addition, since the angle θ differs for each frequency, means for moving the space filter 811 and the photodetector 812 for each frequency is required and the moving distance also increases according to the distance to be diffused. Therefore, it causes the apparatus to become large-sized due to a moving device and a measurement time to increase due to a moving time. Therefore, this means cannot be applied to a compact apparatus.

Solution to Problem

According to the invention, there is provided a terahertz wave measuring apparatus including a pulse laser light generator that generates a pump beam; a seed beam generator that generates a seed beam; a terahertz wave generator on which the pump beam and the seed beam are incident and which generates a terahertz wave; a terahertz wave detector on which the terahertz wave generated from the terahertz wave generator and interacting with a measured object, and the pump beam are incident, and which generates a terahertz wave detection beam; an interference optical system that multiplexes the terahertz wave detection beam and a reference beam having the same wavelength as that of the terahertz wave detection beam, and generates a plurality of interference beams having different phase relationships; a plurality of photodetectors that detect the interference beam; and a signal processing unit that calculates an output of the plurality of photodetectors and outputs an intensity signal and/or a phase signal of the terahertz wave interacting with the measured object.

The terahertz wave generator includes a first nonlinear optical crystal and the terahertz wave is generated by causing the pump beam and the seed beam which is angle-controlled are incident on the first nonlinear optical crystal so as to satisfy a phase matching condition, and the terahertz wave detector includes a second nonlinear optical crystal, and the terahertz wave detection beam is generated by causing the terahertz wave and the pump beam which interact with the measured object are incident on the second nonlinear optical crystal so as to satisfy the phase matching condition.

In one aspect, the terahertz wave measuring apparatus according to the invention uses an idler beam generated from the terahertz wave generator as the reference beam.

In the aspect, it is preferable that the terahertz wave measuring apparatus further including a beam angle controller that controls an incident angle of the seed beam on the terahertz wave generator; and a first incident angle reversing optical system and a second incident angle reversing optical system which emit an incident light at an angle reversed with respect to an optical axis. The first incident angle reversing optical system is disposed in an optical path of the terahertz wave detection beam. The second incident angle reversing optical system is disposed in an optical path of the reference beam. The terahertz wave detection beam and the reference beam are multiplexed on the same optical path in the interference optical system.

In addition, it is preferable that the terahertz wave measuring apparatus further includes an variable optical delay line, and the terahertz wave detection beam and the idler beam passing through the variable optical delay line are multiplexed.

It is preferable that the terahertz wave measuring apparatus further includes a reference photodetector that detects some of the reference beam, and the signal processing unit performs a process of subtracting a variation amount of the reference beam detection signal from an interference beam detection signal by using the reference beam detection signal detected by the reference photodetector and the interference beam detection signal (signal represented by Expression (9) described below) of the interference beam.

In another aspect, the terahertz wave measuring apparatus according to the invention uses a light obtained by being branched from the seed beam generated from the seed beam generator as the reference beam.

Also in the aspect, it is preferable that the terahertz wave measuring apparatus further includes a beam angle controller that controls an incident angle of the seed beam on the terahertz wave generator, and a first incident angle reversing optical system and a second incident angle reversing optical system which emit an incident light at an angle reversed with respect to the optical axis. The first incident angle reversing optical system is disposed in the optical path of the terahertz wave detection beam, the second incident angle reversing optical system is disposed in the optical path of the reference beam, and the terahertz wave detection beam and the reference beam are multiplexed on the same optical path in the interference optical system.

In addition, it is preferable that the terahertz wave measuring apparatus further includes an variable optical delay line, and the terahertz wave detection beam and the reference beam passing through the variable optical delay line are multiplexed.

In addition, it is preferable that the terahertz wave measuring apparatus further includes a reference photodetector that detects some of the reference beam formed of the idler beam. A difference between a reference beam detection signal detected by the reference photodetector and a reference beam standard value acquired in advance is calculated as a variation value, and an intensity signal of the terahertz wave interacting with the measured object is corrected using the variation value.

Advantageous Effects of Invention

According to the invention, it is possible to provide a highly sensitive terahertz wave measuring apparatus. Furthermore, it is possible to improve the sensitivity of a weak signal by separation of the background light, shorten the optical path length, reduce the size, and simplify the apparatus by downsizing a light source, and improve the stability/safety by reducing a light source output.

Problems, constructions, and effects other than those described above will be clarified by the description of the following embodiments.

DESCRIPTION OF EMBODIMENTS

Figure 1:
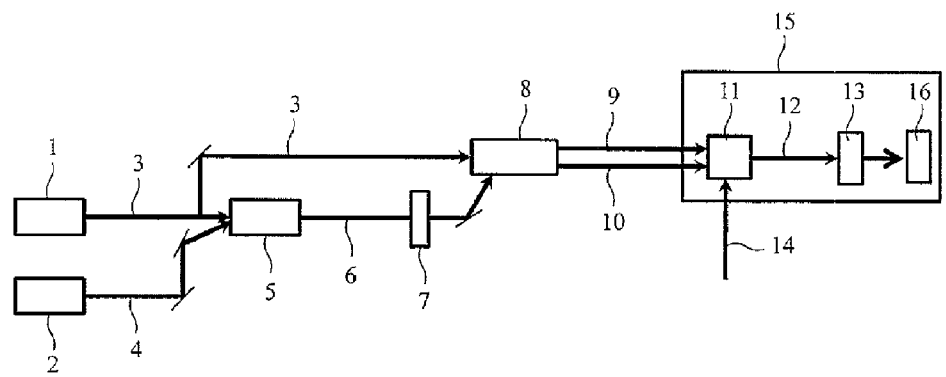
FIG. 1 is a block diagram illustrating an example of a terahertz wave measuring apparatus.

The invention provides a technology that enables terahertz wave measurement with small size and good sensitivity. Representative means for achieving the above object will be explained below.

(1) A terahertz wave is generated by irradiating a nonlinear optical crystal with a pump beam and a seed beam satisfying a phase matching condition. A terahertz wave detection beam is generated by irradiating the nonlinear optical crystal with the pump beam and the terahertz wave transmitted or reflected by a measured object satisfying the phase matching angle. A reference beam having the same wavelength as that of the terahertz wave detection beam is incident on a homodyne/phase diversity detection optical system formed of an interference optical system and a photodetector. Since the terahertz wave detection beam and the reference beam have coherency, interference beam is generated, and a detection signal amplified depending on the intensity of the reference beam is obtained as represented by Expression (9) which is described later. Therefore, weak terahertz wave detection beam can be amplified and sensitivity thereof can be increased.

Furthermore, experimentally confirmed that a background light generated by a terahertz wave detector has a feature that a generation frequency range is wide and the coherency is low. From this feature, it is found that interference of the background light is lower than that of the terahertz wave detection light which has high coherency. Since the interference is low, the background light incident on the homodyne/phase diversity detection optical system is incident on a plurality of photodetectors without interfering with the reference beam. Therefore, an influence of the background light can be removed by subtracting the background light from the interference beam. In the phase diversity detection, an in-phase component is subtracted as represented in Expressions (5) and (8) described later. As a result, a signal due to the background light is separated, and only a signal component of the terahertz wave detection beam is amplified.

Furthermore, it is possible to calculate a phase of the terahertz wave detection beam from a ratio between Sig1 and Sig2 in Expressions (5) and (8) described later. Therefore, a phase difference between the terahertz waves in a case where the measured object is present and in a case where the measured object is removed is obtained from the phase difference between the respective terahertz wave detection beams.

From the above, it is possible to reduce the influence of unnecessary background light generated together with the terahertz wave detection beam, to improve the detection sensitivity, and to output the phase difference of the terahertz wave.

(2) Furthermore, high sensitivity can be achieved by using the idler beam generated by a terahertz wave generator as a reference beam. The idler beam has the same wavelength as that of the seed beam and at the same time is amplified using energy of the pump beam to be output. In the homodyne/phase diversity detection, the interference beam is amplified depending on the intensity of the reference beam, and in view of the fact that the high-intensity reference beam is important, it is newly conceived to utilize a high-intensity idler beam that is not used in the related art and that has the same wavelength as that of the terahertz wave detection beam. The high-intensity idler beam is then used for reference beam for homodyne phase diversity detection. In this case, in order to multiplex the terahertz wave detection beam and the reference beam, it is necessary to make the angle incident on the interference optical system at substantially 90°.

In NPL 2, a configuration is disclosed in which the idler beam is incident on the terahertz wave detector and used for phase detection. With this configuration, the phase of the terahertz wave corresponding to the optical path length can be measured by moving a rooftop mirror, and by observing and recording a change in the intensity of the detection light while changing the optical path length of the terahertz wave. However, since the objective of NPL 2 is not to improve sensitivity but to detect phases, measures concerning sensitivity improvement are not described, and measures to reduce the influence of background light are not illustrated. Furthermore, the following problems occur by causing idler beam to be incident on the terahertz wave detector formed of a nonlinear crystal. When the intensity of the idler beam is larger than that of the terahertz wave, unnecessary light having interference, which is difficult to remove, other than the detection light is generated by the nonlinear effect due to the intensity of the idler beam. Therefore, a sufficient effect of improving sensitivity is not obtained. Conversely, if the idler beam is adjusted to the intensity of a weak terahertz wave so that no nonlinear effect occurs, an amplification effect cannot be obtained because the intensity of the reference beam decreases. Therefore, it is necessary to multiplex the detection light and the reference beam with an optical system that does not generate the nonlinear effect. In addition, in the configuration of NPL 2, a single interference beam generated by matching a polarization surface of the idler beam incident on the terahertz wave detector and a polarization surface of the detection light is observed by a single photodetector. In the present invention, the polarization surface is adjusted and the idler beam is incident on the interference optical system to generate a plurality of interference waves, a plurality of photodetectors are used, and thereby signal intensity can be observed by one measurement irrespective of the phase difference as represented in Expression (9) described later. On the other hand, it is necessary in NPL 2 to move the rooftop mirror and observe the intensity of the plurality of optical path lengths plural times to obtain the signal intensity from the maximum value, resulting in a decrease in measurement speed. Therefore, it is difficult to apply it directly to the configuration of the present invention.

(3) In the terahertz wave measuring apparatus of the is-TPG system of the related art, in a case where the generation/detection frequency is changed, a beam angle controller such as a diffraction grating or a galvano mirror controls a seed beam incident angle to the terahertz wave generator. On the other hand, also in a case of incident on the interference optical system, as described above, it is necessary to be controlled so that the terahertz wave detection beam and the reference beam are always incident at substantially 90 degrees and the optical paths to be multiplexed coincide. Therefore, the angle is controlled so that the terahertz wave detection beam and the reference beam are always irradiated to the photodetector by the incident angle reversing optical system for detection light and the incident angle reversing optical system for reference beam. An emission angle of the terahertz wave detection beam and an emission angle of the reference beam are the same as the incident angle of the seed beam. It is possible to generate terahertz wave detection beam and reference beam converging to a common position by reversing the angle.

For example, it is possible to emit light at an angle that is symmetrical to the incident angle with respect to the optical axis by applying a relay lens configuration as an optical system. It is possible to cause the terahertz wave detection beam and the reference beam to be incident on the interference optical system at an appropriate incident angle only with the control by the beam angle controller by selecting an appropriate NA and focal length.

(4) In order to generate the interference beam, an optical path length difference between the terahertz wave detection beam and the reference beam is appropriately adjusted, and pulses of the terahertz wave detection beam and the reference beam need to overlap each other. The pulse width of the terahertz wave detection beam and the idler beam is shortened from substantially 500 ps of a pulse width of the pump beam by a parametric process, is substantially 100 ps, and corresponds to the optical path length of substantially 30 mm. It is desirable that start positions of pulses of the terahertz wave detection beam and the reference beam coincide with each other within 1 mm. Here, for a minute change in the optical path difference of substantially several hundreds µm, a phase variation component is separated by the phase diversity system, and it is hardly to be affected by an interference beam intensity signal. However, for example, if the optical path length of several millimeters or more is changed due to an external factor such as a difference in dielectric constant of the measurement sample, a variation in an ambient temperature, a change due to transportation or aging of the optical system, or the like, the interference between the terahertz wave detection beam and the reference beam may deteriorate and the intensity of the interference beam may decrease. Therefore, it is possible to generate a constant interference beam by matching the optical path length within 1 mm by installing the variable optical delay line on the optical path of the reference beam. Furthermore, as illustrated in a flowchart of FIG. 8, by automating the optical path length adjustment, stable measurement can be performed and convenience is improved without an operation of a user.

(5) In the terahertz wave measuring apparatus of the present invention, intensity variation of terahertz wave detection beam occurs due to intensity variation of the pump beam and the seed beam incident on the nonlinear optical crystal for terahertz wave generation. Due to the variation, the accuracy of the measurement value may be reduced. The intensity variations of the pump beam and the seed beam are generated inside the pump beam source and the seed beam source, respectively, and it is not easy to suppress the variations from the outside. Therefore, the intensity of the idler beam generated simultaneously with the terahertz wave in a nonlinear optical crystal into which the pump beam and the seed beam are incident is detected using the photodetector, and an amount of variation is observed. Since this idler beam intensity variation occurs in the parametric process like terahertz wave generation, it has high correlation with the intensity variation of terahertz wave. The variation component from an average value of the intensity of the idler beam is subtracted from a detection signal value of the intensity of the interference beam while considering an intensity ratio between the interference beam detection signal and the idler beam detection signal. Then it is possible to reduce the variation of the detection light signal caused by the generation of the terahertz wave and to measure changes in the detected optical signal caused by the measurement sample with high accuracy.

(6) In addition, it is also possible to increase the sensitivity by using the seed beam irradiated from a seed beam source instead of the idler beam generated by the terahertz wave generator as the reference beam. It is possible to obtain a stable interference beam without being influenced by variation of pump beam intensity by using a stable seed beam generated by the seed beam source. However, since it is necessary to control the incident angle in order to multiplex the terahertz wave detection beam and the reference beam, a beam splitter is inserted between the beam angle controller and a terahertz wave generation-side nonlinear optical crystal, so that the seed beam is branched and becomes the reference beam.

(7) It is possible to generate the terahertz wave detection beam and the reference beam converging to a common position by reversing the angle change caused by the beam angle controller of the seed beam branched by the beam splitter. For example, it is possible to emit the light at an angle symmetrical to the incident angle with respect to the optical axis by applying the relay lens configuration as the optical component. It is possible to cause the terahertz wave detection beam and the reference beam to be incident on the interference optical system at an appropriate incident angle only with the control by the beam angle controller by selecting an appropriate NA and focal length.

Figure 8:
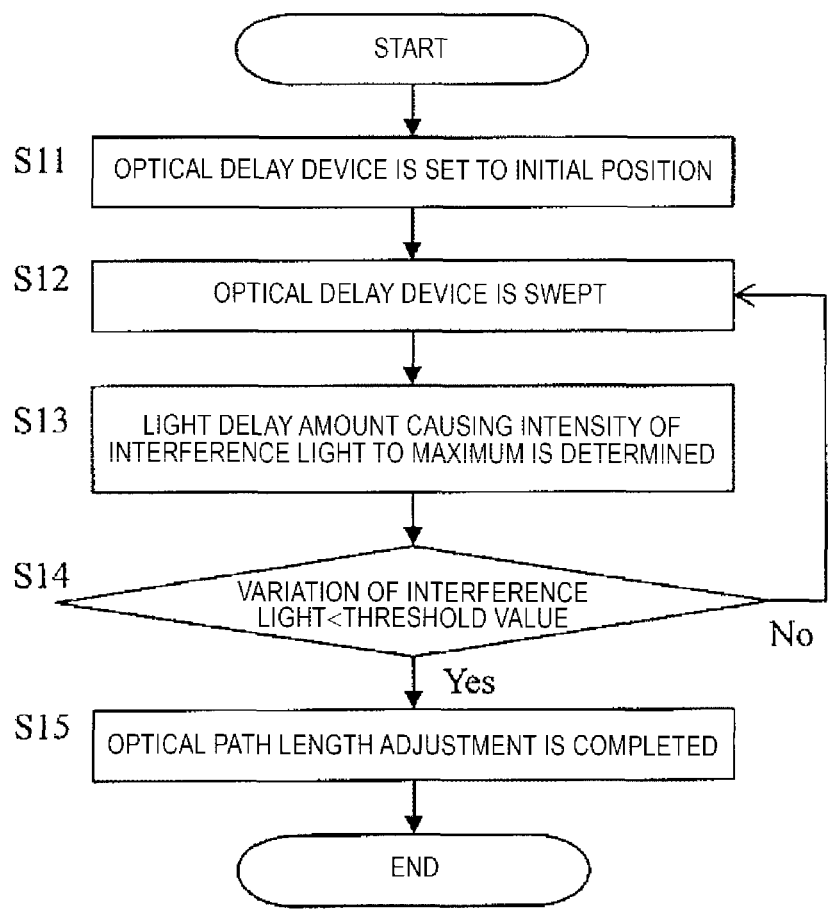
FIG. 8 is a flowchart illustrating a procedure of an optical path length adjustment.

(8) Even in a case where the seed beam is used as the reference beam, in order to generate the interference beam, the optical path lengths of the terahertz wave detection beam and the reference beam are appropriately adjusted, the pulses of the terahertz wave detection beam and the reference beam overlap each other, and it is necessary to maintain the interference. For example, the optical path length can be changed and the interference can be deteriorated due to external factors such as a difference in dielectric constant of the measurement sample, a variation in the ambient temperature, a change due to transportation or aging of the optical system, or the like. Therefore, it is possible to cause the optical path length to coincide and to generate a constant interference beam by installing the variable optical delay line on the optical path of the reference beam branched from the seed beam. Furthermore, stable measurement can be performed without an operation of a user, and convenience is improved by automating the optical path length adjustment as illustrated in the flowchart of FIG. 8.

(9) Since the beam splitter branching the seed beam is installed between the nonlinear optical crystal and the beam angle controller, the beam splitter is close to the optical path of the pump beam. The angle between the pump beam and the seed beam is substantially 1° to 3°, and there is a possibility that both the seed beam and the pump beam pass through the interior of the beam splitter. In this case, it is possible cause the pump beam to pass through the beam splitter and to branch only the seed beam by causing the seed beam to pass through the λ/2 wavelength plate to cause the angle between the polarization surfaces of the pump beam and the seed beam to be substantially 90 degrees. With this configuration, it is possible to bring the beam splitter, the nonlinear optical crystal, and the beam angle controller to close to each other, and it is possible to downsize the apparatus.

(10) In the homodyne phase diversity detection, the terahertz wave detection beam interferes with reference beams of four phases of 0°, 90°, 180°, and 270°. The four generated interference beams are respectively represented by Expressions (3), (4), (6) and (7) described later. The difference between interference beams at 0° and 180° is represented by Expression (5), the difference between the interference beams at 90° and 270° is represented by Expression (8), and the intensity of the interference beam represented by Expression (9) is obtained from a sum of squares of the respective values. Therefore, it is possible to easily and stably observe the intensity signal without adjusting the optical path length within an interference distance range (substantially several mm) between the terahertz wave detection beam and the reference beam.

Hereinafter, embodiments of the invention will be described with reference to the drawings.

Example 1

FIG. 1 is a block diagram illustrating a first example of a terahertz wave measuring apparatus of the invention.

Figure 18:
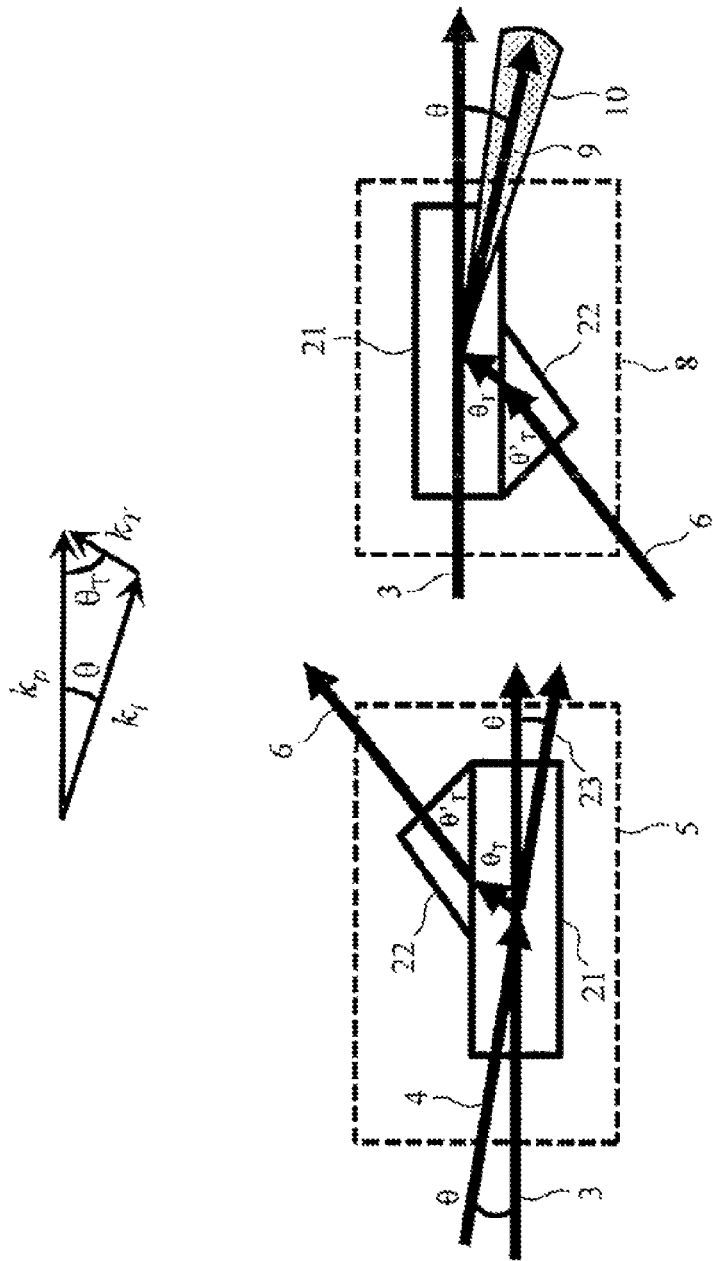
FIG. 18 is a schematic diagram illustrating a configuration of a terahertz wave generator and a terahertz wave detector, and a direction of each light and a terahertz wave.
Figure 19:
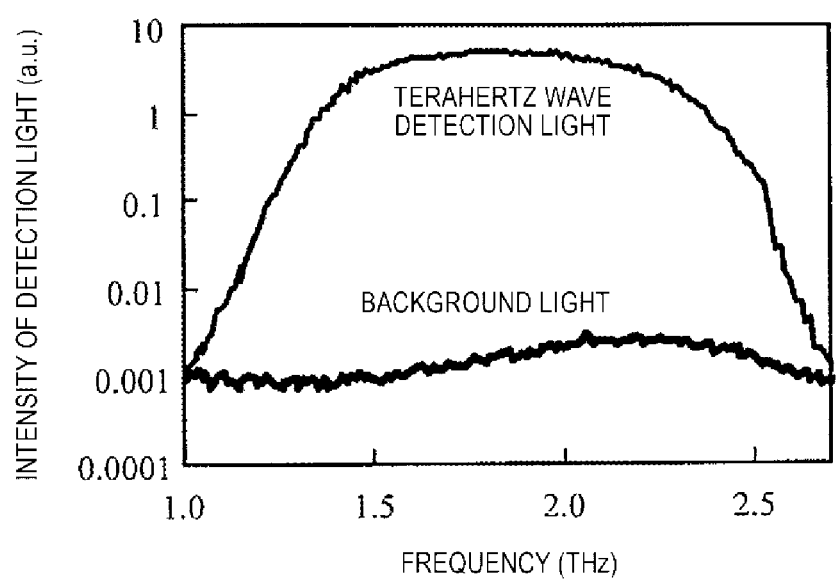
FIG. 19 is a graph illustrating an intensity difference of an intensity of detection light and an intensity of a background light measured using a system of the related art.

A pump beam generator 1 is configured of a pulse laser light source and an optical amplifier inserted into an optical path for improving an intensity, and generates a pump beam 3 of substantially 18 mJ with a wavelength of substantially 1064 nm and a pulse width of substantially 500 ps. The pump beam is incident on a terahertz wave generator 5 and a terahertz wave detector 8 respectively. As illustrated in FIG. 18, the terahertz wave generator and the terahertz wave detector are configured of a nonlinear optical crystal 21 and a silicon prism 22. As the nonlinear optical crystal, for example, MgO:LiNbO$_3$ is used. On the other hand, the seed beam generator 2 is configured of a continuous wave variable wavelength laser light source and an optical amplifier, and generates a seed beam 4 of 1068 nm to 1075 nm, and substantially 100 to 500 mW. The seed beam 4 is incident on the terahertz wave generator 5 at an angle satisfying a phase matching condition with the pump beam 3. In the terahertz wave generator 5, a terahertz wave 6 generated by a parametric process interacts with a measured object 7, that is, transmits or reflects on the measured object 7, and is incident on the terahertz wave detector 8.

In the terahertz wave detector 8, a terahertz wave detection beam 9 depending on the intensity and the wavelength of the incident terahertz wave is generated by the parametric process. In addition, simultaneously, a background light 10 not depending on the terahertz wave is generated. The terahertz wave detection beam 9 and the background light 10 are incident on an interference optical system 11 configuring a homodyne/phase diversity detection optical system 15. In addition, a reference beam 14 having the same wavelength as that of the terahertz wave detection beam 9 is also incident on the interference optical system 11. In the interference optical system 11, the terahertz wave detection beam 9 and the reference beam 14 are multiplexed on the same optical path using, for example, a beam splitter or a beam combiner. Next, a plurality of phases are generated in the reference beam and a plurality of interference beams 12 generated by an interaction between the terahertz wave detection beam and the reference beam of the plurality of phases are incident on a plurality of photodetectors 13. For example, four kinds of the interference beams having different phase relationships by 90 degrees between a signal light and the reference beam are generated, are respectively detected by four photodetectors, and an obtained interference signal is signal-processed by a signal processing unit 16. Therefore, an in-phase component and a phase component are removed, and an amplified intensity signal is obtained.

Figure 2:
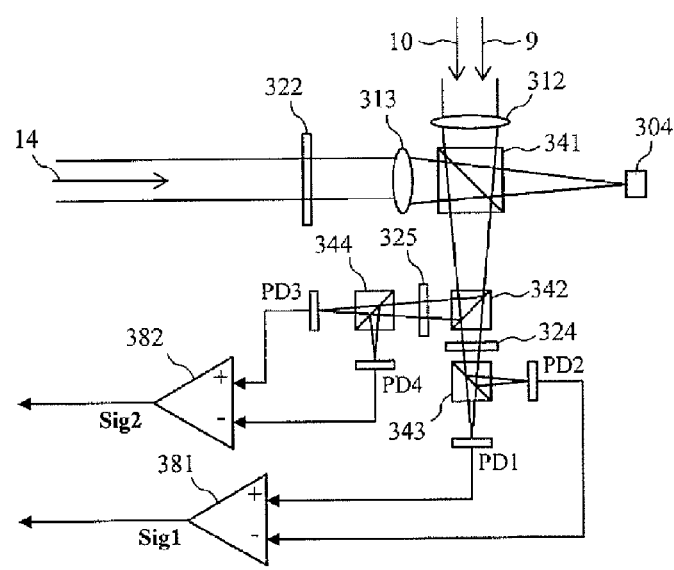
FIG. 2 is a schematic diagram illustrating a configuration example of a homodyne/phase diversity detection optical system.

FIG. 2 is a schematic diagram illustrating a configuration example of a homodyne/phase diversity detection optical system. The terahertz wave detection beam 9 and the background light 10 are condensed by a first condenser lens 312, transmits a first polarization beam splitter 341, and then heads in a direction of a half beam splitter 342. The reference beam 14 transmits a λ/2 plate 322 and thereby a polarization direction is rotated at an arbitrary angle depending on an installation angle of the λ/2 plate 322, and the reference beam 14 is converted into a linear polarization light crossing with the terahertz wave detection beam at an arbitrary angle. A polarization component orthogonal to the terahertz wave detection beam is condensed by a second condenser lens 313, and then is reflected by the first polarization beam splitter 341, and is composed with the signal light, thereby heading in a direction of the half beam splitter 342.

On the other hand, the polarization component parallel to the terahertz wave detection beam transmits the polarization beam splitter 341 and is incident on a variation monitor photodetector 304. A detected signal is used for signal processing of a variation control as described in a fourth example and a seventh example in detail.

A combined light of the terahertz wave detection beam and the reference beam orthogonal to each other transmits the half beam splitter 342 which is a half mirror, is rotated by 45 degrees in the polarization direction by a λ/2 plate 324, and then is separated into an orthogonal linear polarization light by a polarization beam splitter 343 and is detected by a first photodetector PD1 and a second photodetector PD2. In this case, signals detected by the PD1 and PD2 are represented by Expressions (3) and (4).

$$I_{PD1} = \left|\frac{1}{2}E_{sig} + \frac{1}{2}E_{ref}\right|^2 \quad (3)$$
$$= \frac{1}{4}|E_{sig}|^2 + \frac{1}{4}|E_{ref}|^2 + \frac{1}{2}|E_{sig}||E_{ref}|\cos(\phi_{sig} - \phi_{ref})$$

$$I_{PD2} = \left|\frac{1}{2}E_{sig} - \frac{1}{2}E_{ref}\right|^2 \quad (4)$$
$$= \frac{1}{4}|E_{sig}|^2 + \frac{1}{4}|E_{ref}|^2 - \frac{1}{2}|E_{sig}||E_{ref}|\cos(\phi_{sig} - \phi_{ref})$$

Here, $E_{sig}$ is an amplitude of the signal light (terahertz wave detection beam), $E_{ref}$ is an amplitude of the reference beam, $\phi_{sig}$ is a phase of the signal light, and $\phi_{ref}$ is a phase of the reference beam. For the sake of simplicity, $E_{sig}$ and $E_{ref}$ are assumed to be fully coherent.

Outputs of PD1 and PD2 are input into a differential circuit 381 and a differential signal Sig1 represented in Expression (5) is generated.

$$Sig1 = I_{PD1} - I_{PD2} = |E_{sig}||E_{ref}|\cos(\phi_{sig} - \phi_{ref}) \quad (5)$$

Another part of the combined light is reflected by the half beam splitter 342 and is converted into a circular polarization light by a λ/4 plate 325 which is disposed by rotating substantially 45° with respect to polarization directions of the signal light and the reference beam. In this case, since original polarization directions of the signal light and the reference beam are different from each other by substantially 90 degrees, the combined light is changed to a circular polarization light in a reversed rotation direction. The circular polarization light is separated into an orthogonal linear polarization light by a polarization beam splitter 344 and signals represented by Expressions (6) and (7) are detected by a third photodetector PD3 and a fourth photodetector PD4.

$$I_{PD3} = \frac{1}{8}|(1-i)E_{sig} + (1+i)E_{ref}|^2 \quad (6)$$
$$= \frac{1}{4}|E_{sig}|^2 + \frac{1}{4}|E_{ref}|^2 + \frac{1}{2}|E_{sig}||E_{ref}|\sin(\phi_{sig} - \phi_{ref})$$

$$I_{PD4} = \frac{1}{8}|(1+i)E_{sig} + (1-i)E_{ref}|^2 \quad (7)$$
$$= \frac{1}{4}|E_{sig}|^2 + \frac{1}{4}|E_{ref}|^2 - \frac{1}{2}|E_{sig}||E_{ref}|\cos(\phi_{sig} - \phi_{ref})$$

Outputs of PD3 and PD4 are input into a differential circuit 382 and a differential signal Sig2 represented by Expression (8) is generated.

$$Sig2 = I_{PD3} - I_{PD4} = |E_{sig}||E_{ref}|\sin(\phi_{sig} - \phi_{ref}) \quad (8)$$

The differential signals Sig1 and Sig2 generated as described above are processed by the signal processing unit 16 of FIG. 1. The signal processing unit 16 samples and digitizes Sig1 and Sig2 at the time of input, and performs subsequent processing by digital calculation. That is, the processing of Expression (9) is performed by the digital calculation. Thus, regardless of the phase difference ($\phi_{sig} - \phi_{ref}$), an intensity signal S proportional to the intensity $|E_{sig}|^2$ of the signal light is obtained.

$$S=(Sig1)^2+(Sig2)^2=|E_{sig}|^2|E_{ref}|^2 \qquad (9)$$

It is possible to observe frequency dependency of a change amount of the terahertz wave generated by transmission or reflection of the measured object, for example, an absorption spectrum waveform, by recording a relationship between the frequency $f_T$ of the terahertz wave and the intensity signal. It is possible to apply the terahertz wave as a spectrometric apparatus by the configuration. Further, it is possible to provide an apparatus for detecting a thickness of a layer of the measured object, imaging the surface shape and internal structure, and measuring the refractive index based on the detected phase difference information.

In the phase diversity detection optical system, by using the reference beam with a plurality of phase differences, the intensity signal becomes constant even in a case where the phases of the terahertz wave detection beam and the reference beam are different. Therefore, it is unnecessary to insert a mechanical optical path length and it is possible to reduce the size and increase the speed. Furthermore, since the background light does not interfere with the reference beam, it is incident on a plurality of photodetectors as the same phase component with the same intensity. Since the in-phase component is removed by a calculation processing of the signal processing unit 16, the signal component of the background light is separated and only the intensity and the phase of the terahertz wave detection beam are output. With the configuration described above, it is possible to realize a small and highly sensitive terahertz wave measuring apparatus.

In the optical system illustrated in FIG. 2, the four photodetectors PD1 to PD4 detect interference beams in which the interference phases of the terahertz wave detection beam and the reference beam differ from each other by an integer multiple of substantially 90 degrees. Then, the calculations of Expressions (5) and (8) are performed by inputting, to the differential circuits 381 and 382, the outputs of the pair of photodetectors PD1 and PD2, and PD3 and PD4 for detecting the interference beam where the interference phases of the terahertz wave detection beam and the reference beam are mutually different by substantially 180°. Here, the photodetector PD1 and the photodetector PD2 may be replaced by one current differential type photodetector, the photodetector PD3 and the photodetector PD4 may be replaced by one current differential type photodetector.

Figure 3:
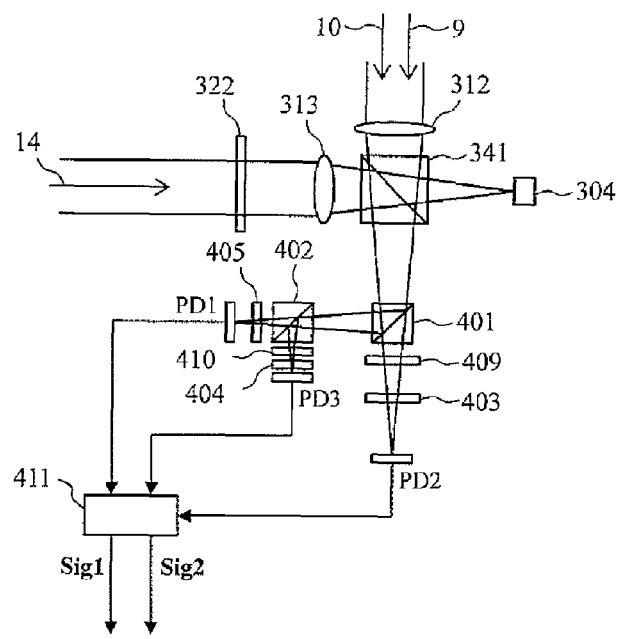
FIG. 3 is a schematic diagram illustrating a configuration example of the homodyne/phase diversity detection optical system.

The number of detectors constituting the homodyne/phase diversity detection optical system and the phase difference between the signal light and the reference beam on each detector are not necessarily limited to the above description. FIG. 3 is a schematic diagram illustrating another configuration example of a homodyne/phase diversity detection optical system. Here, three detectors are used, and a configuration example in a case where the phase difference between the signal light and the reference beam is substantially 0 degree, substantially 120 degrees, and substantially 240 degrees on each detector is illustrated.

The light passing through the condenser lens 312 is divided into three light fluxes by non-polarization beam splitters 401 and 402, and after passing through the polarizers 403, 404, and 405 which transmit a 45-degree polarization light, respectively, the light is detected by the detector PD1, PD2, and PD3. A phase plate 409 that generates a phase difference of 60 degrees between the signal light and the reference beam is inserted into one of the three light fluxes, and a phase plate 410 that generates a phase difference of 300 degrees between the signal light and the reference beam is inserted into another one of the three light flux. Further, the non-polarization beam splitter 401 has a ratio of the transmittance to the reflectance of 1:2 so that the light amounts on the detectors respectively become equal to each other, and the non-polarization beam splitter 402 has the transmittance equal to the reflectance. In this case, intensities $I_{PD1}$, $I_{PD2}$, and $I_{PD3}$ of the light incident on each detector are represented by the following expressions.

$$I_{PD1} = \left| \frac{1}{\sqrt{3}}E_{sig} - \frac{1}{\sqrt{3}}E_{ref} \right|^2 \qquad (10)$$
$$= \frac{1}{3}|E_{sig}|^2 + \frac{1}{3}|E_{ref}|^2 - \frac{2}{3}|E_{sig}||E_{ref}|\cos(\phi_{sig}-\phi_{ref})$$

$$I_{PD2} = \left| \frac{1}{\sqrt{3}}E_{sig} + \frac{1}{\sqrt{3}}e^{\frac{\pi}{3}i}E_{ref} \right|^2 \qquad (11)$$
$$= \frac{1}{3}|E_{sig}|^2 + \frac{1}{3}|E_{ref}|^2 + \frac{2}{3}|E_{sig}||E_{ref}|\cos\left(\phi_{sig}-\phi_{ref}-\frac{\pi}{3}\right)$$

$$I_{PD3} = \left| \frac{1}{\sqrt{3}}E_{sig} + \frac{1}{\sqrt{3}}e^{-\frac{\pi}{3}i}E_{ref} \right|^2 \qquad (12)$$
$$= \frac{1}{3}|E_{sig}|^2 + \frac{1}{3}|E_{ref}|^2 + \frac{2}{3}|E_{sig}||E_{ref}|\cos\left(\phi_{sig}-\phi_{ref}+\frac{\pi}{3}\right)$$

However, it is considered that a phase difference of 180 degrees occurs between the signal light and the reference beam at the time of reflection in the non-polarization beam splitters 401 and 402. Next, these output signals are input into the calculation circuit 411, and the following outputs Sig1 and Sig2 are generated.

$$Sig1 = I_{PD1} - \frac{I_{PD2}+I_{PD3}}{2} = |E_{sig}||E_{ref}|\cos(\phi_{sig}-\phi_{ref}) \qquad (13)$$

$$Sig2 = \frac{\sqrt{3}}{2}(I_{PD2}-I_{PD3}) = |E_{sig}||E_{ref}|\sin(\phi_{sig}-\phi_{ref}) \qquad (14)$$

Then, these have the same shape as the differential signals Sig1 and Sig2 in the example of the four detectors illustrated in FIG. 2. Therefore, the intensity signal S not depending on the phase difference between the signal light and the reference beam can be obtained by the following calculation.

$$S=(Sig1)^2+(Sig2)^2=|E_{sig}|^2|E_{ref}|^2 \qquad (15)$$

Example 2

Figure 4:
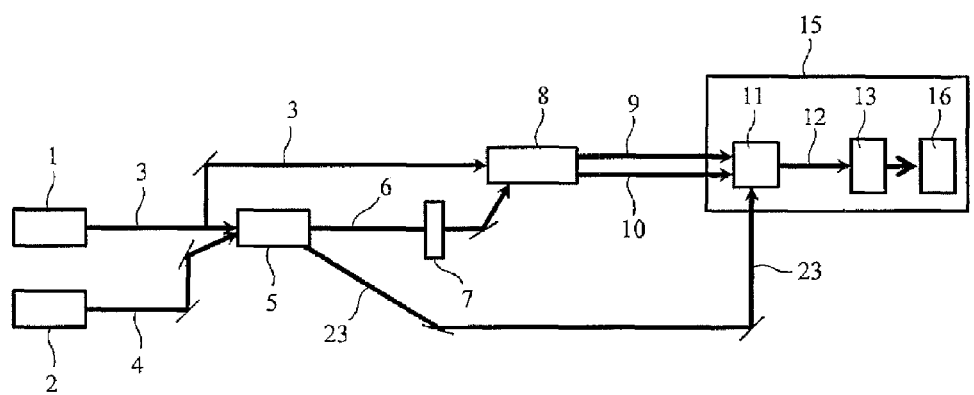
FIG. 4 is a block diagram illustrating an example of the terahertz wave measuring apparatus.

FIG. 4 is a block diagram illustrating a second example of a terahertz wave measuring apparatus of the invention.

As illustrated in FIG. 18, the terahertz wave generator 5 generates the idler beam 23 at the same time as the terahertz wave 6. As illustrated in PTL 2, the terahertz wave and the idler beam are generated in a parametric process in which one pump photon disappears and one idler beam photon and one terahertz wave photon are generated. Therefore, there is a strong correlation between the intensity of the terahertz wave and the intensity of the idler beam. Further, the frequency $f_i$ of the idler beam is a difference frequency between the pump beam frequency $f_p$ and the terahertz wave frequency $f_T$, and coincides with the frequency of the terahertz wave detection beam 9. Also, since the idler beam is generated by the parametric process, it is higher in intensity than the seed beam. Therefore, the idler beam 23 generated from the terahertz wave generator 5 is incident on the interference optical system 11 as the reference beam.

Since the signal intensity of the interference beam increases in proportion to the intensity of the reference beam according to the principle of homodyne detection represented in the Expression (9), a weak signal can be amplified and to be high sensitivity by using the intense idler beam as the reference beam. Since the idler beam is a light which is not used in the related art, it is unnecessary to increase the area of the apparatus required for generating the reference beam or to add a light source, and it is possible to reduce the size and cost of the apparatus.

Example 3

Figure 5:
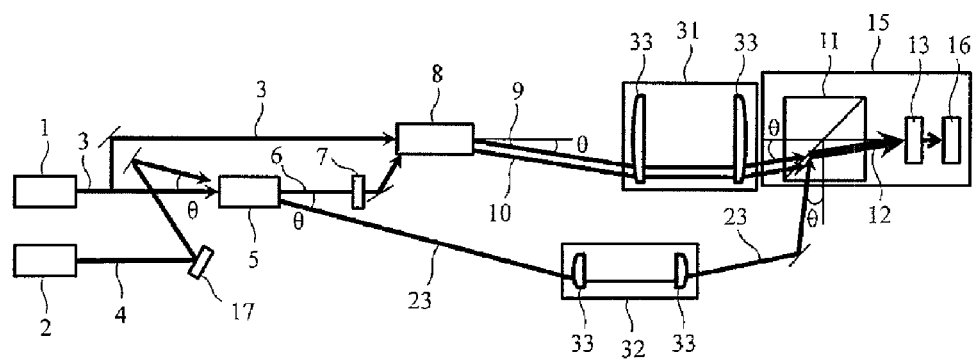
FIG. 5 is a block diagram illustrating an example of the terahertz wave measuring apparatus.

FIG. 5 is a block diagram illustrating a third example of a terahertz wave measuring apparatus of the invention.

A seed beam 4 is incident on a terahertz wave generator 5 at an angle θ with a pump beam 3 via a beam angle controller 17 to satisfy a phase matching condition. The angle θ is controlled by the beam angle controller 17 together with a wavelength of the incident seed beam so that it increases monotonically almost in proportion to a terahertz wave frequency. For example, diffraction grating or a galvano mirror can be used for the beam angle controller 17. A terahertz wave 6 emitted from the terahertz wave generator 5 transmits or reflects on a measured object 7, and is incident on a terahertz wave detector 8 together with a pump beam 3. In the terahertz wave detector 8, a terahertz wave detection beam 9 depending on the intensity and the wavelength of the incident terahertz wave is generated by a parametric process. The terahertz wave detection beam 9 is irradiated from the terahertz wave detector 8 in a direction forming an angle θ with the incident pump beam 3. The angle θ is the same as the angle θ formed by the pump beam and the seed beam incident on the terahertz wave generator 5.

The terahertz wave detection beam 9 is incident on an interference optical system 11 at an angle θ by a detection beam incident angle reversing optical system 31. The detection beam incident angle reversing optical system 31 is an optical system that emits an incident light at an angle θ reversed with respect to the optical axis and, for example, can reverse an angle by a configuration in which two relay lenses 33 are combined. In addition, a reference idler beam 23 is also irradiated in a direction of the angle θ formed with the same pump beam. The idler beam 23 as the reference beam is incident on the interference optical system 11 at an angle θ by a reference beam incident angle reversing optical system 32 that emits the incident light at an angle reversed with respect to the optical axis.

Figure 6:
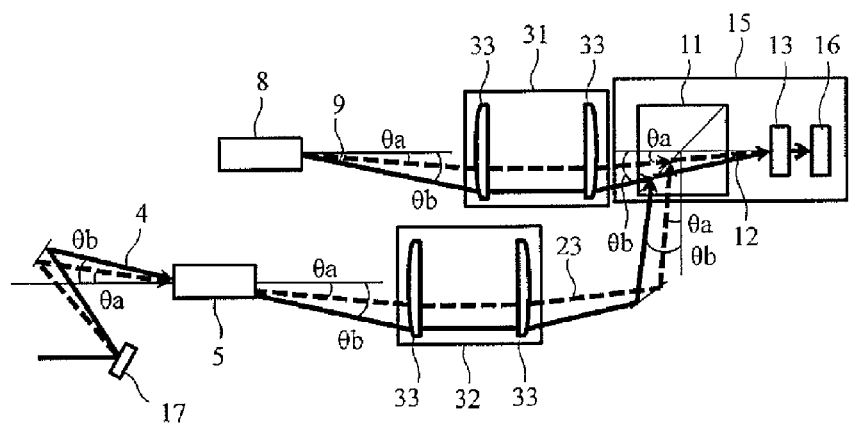
FIG. 6 is a diagram illustrating a change in an optical path in a case where a control angle θ is changed.

FIG. 6 is a diagram illustrating a change in the optical path in a case where a control angle θ is changed. In a case where the seed beam 4 is incident on the terahertz wave generator 5 at an angle θa at which the terahertz wave frequency is lowered by controlling the beam angle controller 17, the terahertz wave detection beam 9 travels along the optical path indicated by a broken line, passes through the interference optical system 11 at the angle θa reversed by the incident angle reversing optical system 31, and is incident on a photodetector 13. On the other hand, the idler beam 23 is also emitted from the terahertz wave generator 5 at the angle θa, travels along the optical path indicated by the broken line, and is incident on the interference optical system 11 at the angle θa reversed by the incident angle reversing optical system 32. The idler beam 23 is reflected by a reflection surface of the beam splitter used in the interference optical system 11 and overlaps on the same optical path as the terahertz wave detection beam 9 to generate the interference beam 12 and is incident on the photodetector 13.

Next, in a case where the seed beam 4 is incident on the terahertz wave generator 5 by controlling the beam angle controller 17 so that so as to be an angle θb at which the terahertz wave frequency becomes higher, the terahertz wave detection beam 9 and the idler beam 23 travel on the optical path indicated by a solid line, respectively, and are incident on the interference optical system 11 at the angle θb reversed by the incident angle reversing optical system 31 and the incident angle reversing optical system 32. The terahertz wave detection beam 9 passing through the reflection surface of the beam splitter used in the interference optical system 11 and the idler beam 23 reflected by the reflection surface travel on the same optical path and interference beam 12 is generated.

As illustrated in the above operation, the incident angle reversing optical systems 31 and 32 are respectively disposed in the optical path of the terahertz wave detection beam 9 and the optical path of the idler beam 23 as the reference beam. Therefore, the terahertz wave detection beam and the idler beam are multiplexed on the same optical path irrespective of the angle θ in the interference optical system 11 to generate an interference beam, and homodyne/phase diversity detection can be performed. This facilitates the measurement of a transmission spectrum and a reflection spectrum of the measured object. That is, in the spectral measurement, the incident angle θ of the seed beam 4 to the terahertz wave generator 5 is swept so that the terahertz wave generated from the terahertz wave generator 5 is frequency-swept. In this case, the emission angle θ of the idler beam 23 generated from the terahertz wave generator 5 and the emission angle θ of the terahertz wave detection beam 9 generated from the terahertz wave detector 8 are similarly swept, and the angle θ is temporally changed. According to the example, all incident angles can be controlled by controlling only the beam angle controller 17. Therefore, the terahertz wave detection beam and the reference beam can be multiplexed on the same optical path in the interference optical system 11, and spectrum measurement can be performed by the homodyne/phase diversity detection. Therefore, it is possible to construct a compact and stable system.

Example 4

Figure 7:
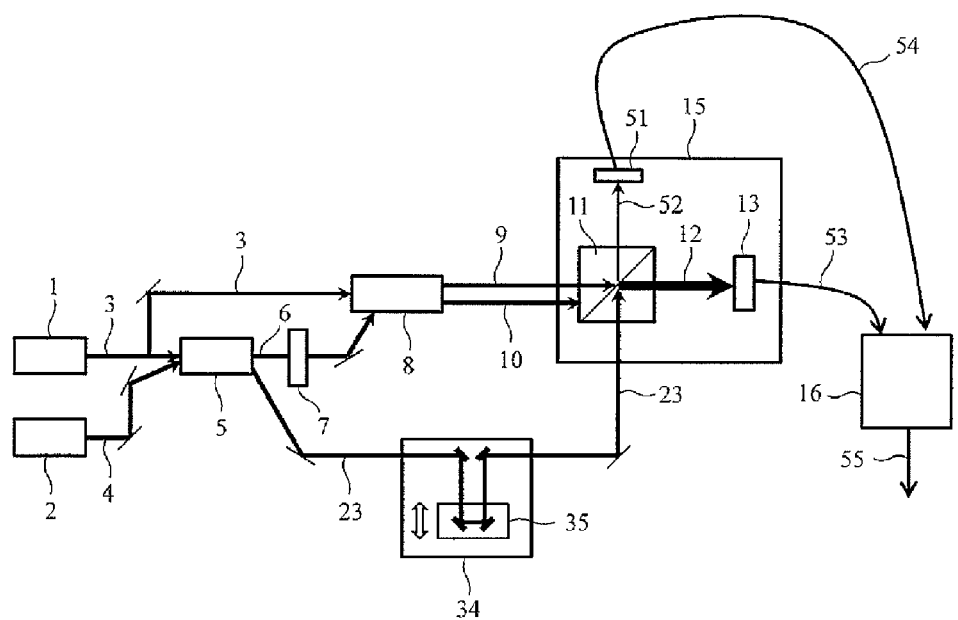
FIG. 7 is a block diagram illustrating an example of the terahertz wave measuring apparatus.

FIG. 7 is a block diagram illustrating a fourth example of a terahertz wave measuring apparatus of the invention.

In order to generate the interference beam, it is necessary to suitably adjust an optical path length difference between a terahertz wave detection beam 9, which is a pulsed light, and an idler beam 23 as a reference beam, and to multiplex them within a pulse width range. For example, if the difference in the optical path length between the terahertz wave detection beam and the reference beam is expanded due to a difference in a dielectric constant of a measured object, a change in an ambient temperature, a change due to transportation or aging of an optical system, or the like, there is a possibility that coherency deteriorates due to a difference in frequency and phase between the terahertz wave detection beam and the reference beam at a position to be multiplexed. Therefore, the idler beam 23 is made incident on an variable optical delay line 34, and the idler beam 23 of which the optical path length is appropriately adjusted by the variable optical delay line 34 is incident on an interference optical system 11 as the reference beam.

As an example of the variable optical delay line 34, an optical delay device as described below can be used. Two mirrors, each having a reflection surface of substantially 45° with respect to the optical path, are installed on a stage 35, and two mirrors having a reflection surface of substantially 45° with respect to the optical path are also formed on the optical path of the reference beam, and the optical path is formed in a U-shape. The optical path length can be arbitrarily adjusted by simultaneously moving the two mirrors on the stage 35 with respect to the two mirrors fixed on the optical path of the reference beam. With this configuration, it is possible to adjust the optical path length difference between the terahertz wave detection beam and the reference beam within a certain range, and to generate a stable interference beam.

FIG. 8 is a flowchart illustrating an example of a procedure of an optical path length adjustment. In a case where the external factor described above causing a large change in the optical path length occurs, the operation illustrated in the flowchart of FIG. 8 is performed. First, the stage 35 of the optical delay device serving as the variable optical delay line 34 is moved to return to an origin point and then moved to an initial position of the optical delay device (S11). Next, while moving the stage 35 of the optical delay device, an interference beam signal 53 output from the photodetector 13 is observed, and the relation between the stage position and the interference beam intensity is recorded (S12). In this case, as a reference, a sample-free state or a standard sample is set as the measured object. A signal processing unit 16 calculates the stage position at which the intensity of the interference beam expressed by Expression (9) is maximum, and moves the stage 35 to that position (S13). In order to reduce the influence of high frequency variation of optical path length due to external factors and obtain a certain accuracy, the interference beam intensity is measured a plurality of times with the same reference as S12 as the measured object. In a case where the variation of the interference beam intensity measured at this time exceeds a threshold range, for example ±1%, S12 is executed again (S14). The variation of the interference beam intensity is calculated each time S12 to S14 are repeated, and the optical path length adjustment is completed if it is within the threshold range (S15). In a case where the value does not fall below the threshold value, the threshold value is changed, and the optical path adjustment is completed at a position where the variation of the interference beam intensity becomes the minimum value.

Figure 16:
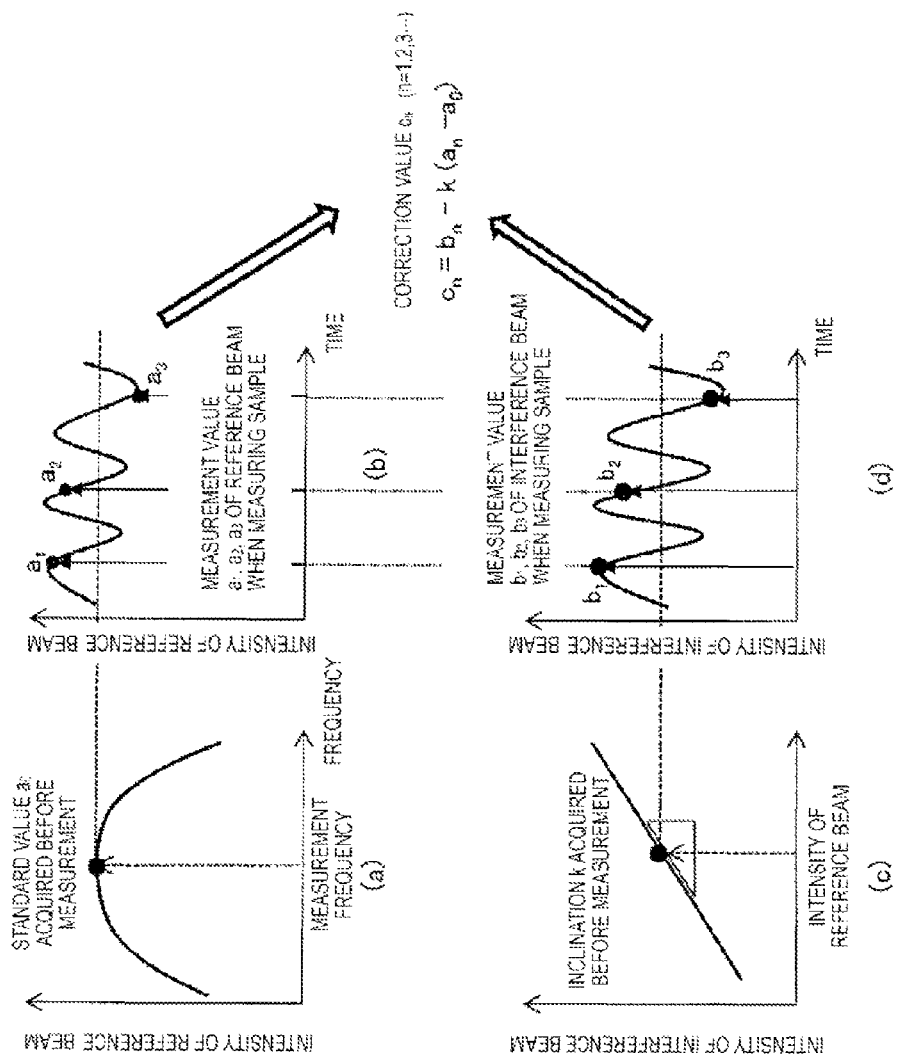
FIG. 16 is a graph illustrating a method of correction calculation for reducing a measurement value variation.
Figure 17:
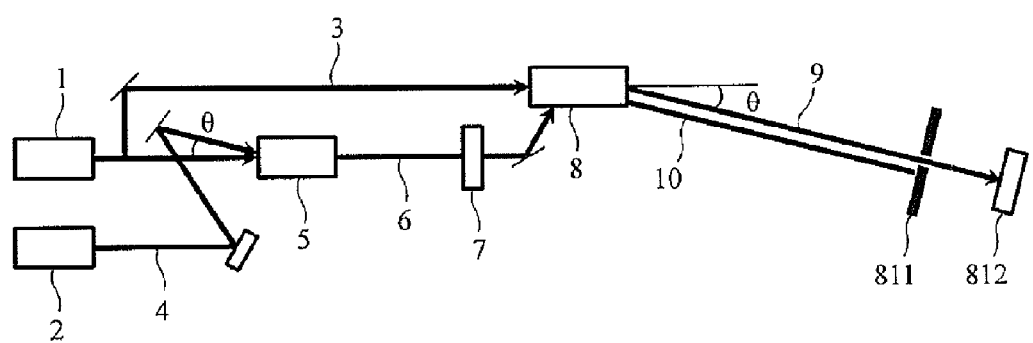
FIG. 17 is a diagram illustrating a configuration of a terahertz wave measuring apparatus of the related art.

Further, FIG. 7 illustrates a configuration for extracting variation components due to a light source or an optical amplifier which are a generation portion of the pump beam or the seed beam, and for reducing it from the interference beam, in order to stabilize the interference beam. Some of the reference beam 52 passing through the interference optical system 11 is detected by the photodetector 51 and the reference beam signal 54 is output to the signal processing unit 16. In addition, the interference beam signal 53 in which the interference beam 12 is detected by the photodetector 13 is output to the signal processing unit 16. As an example of signal processing, a calculation method is illustrated in FIG. 16. Here, the interference beam intensity is a signal calculated by Expression (9) inside the signal processing unit 16. As illustrated in FIG. 16(a), a reference beam signal standard value $a_0$ is acquired for each frequency before sample measurement or before product shipment. A difference between a reference beam intensity measurement value $a_n$ (n=1, 2, 3, . . . ) at the time of sample measurement illustrated in FIG. 16(b) and the standard value is calculated to obtain a variation value. Further, the dependence of the interference beam and the reference beam illustrated in FIG. 16(c) is measured beforehand and an inclination k thereof is calculated. In order to improve the accuracy, it may be acquired for each measurement frequency. The variation component is subtracted from the interference beam intensity $b_n$ at the sample measurement illustrated in FIG. 16(d) by using Expression (16), and the interference beam intensity signal from which the variation component is removed is output as a variation reducing interference beam signal 55.

$$c_n = b_n - k(a_n - a_0) \qquad (16)$$

According to the example, it is possible to reduce the variation caused by the light source or the optical amplifier and to improve measurement accuracy.

Example 5

Figure 9:
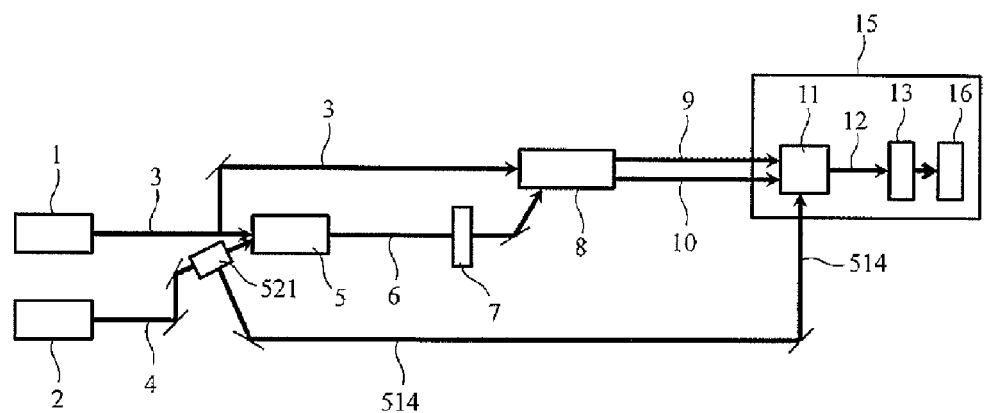
FIG. 9 is a block diagram illustrating an example of the terahertz wave measuring apparatus.

FIG. 9 is a block diagram illustrating a fifth example of a terahertz wave measuring apparatus of the invention.

In the terahertz wave measuring apparatus of Example 1, some of the seed beam 4 incident on the terahertz wave generator 5 is branched as a reference seed beam 514 by a beam splitter 521 installed on the optical path of the seed beam 4. The branched reference seed beam 514 is incident on the interference optical system 11. A frequency $f_s$ of the seed beam 4 is a difference between a pump beam frequency $f_p$ and a terahertz wave frequency $f_T$ and coincides with the frequency of the terahertz wave detection beam 9. Therefore, when the reference seed beam 514 obtained branching the seed beam 4 is multiplexed with the terahertz wave detection beam 9, the interference beam 12 is generated. Although the intensity of the seed beam decreases as compared with the idler beam, the intensity and the phase are the light branched from the seed beam generator 2, which has higher stability than the idler beam which is easily affected by the variation of the pump beam by the interaction with the pump beam.

Therefore, according to the example, a stable interference beam is generated without being strongly influenced by the variation of the pump beam intensity, and stable measurement can be performed by using a relatively stable seed beam as the reference beam.

Example 6

Figure 10:
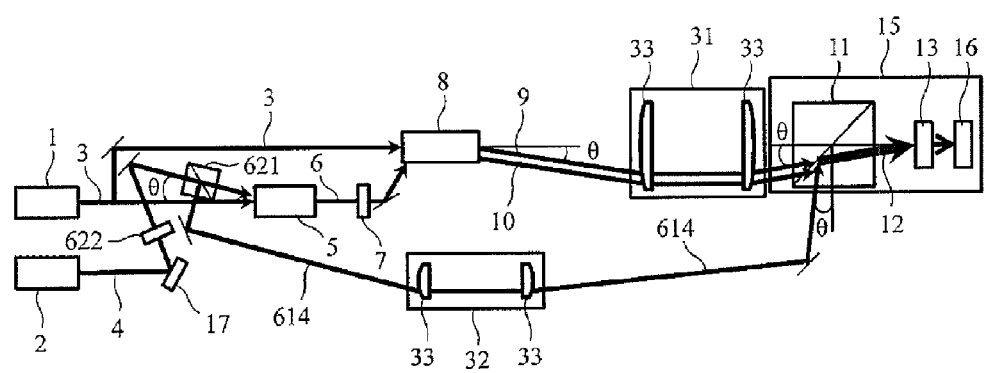
FIG. 10 is a block diagram illustrating an example of the terahertz wave measuring apparatus.

FIG. 10 is a block diagram illustrating a sixth example of a terahertz wave measuring apparatus of the invention.

In a terahertz wave measuring apparatus of Example 5, a beam angle controller 17 controls an angle of a seed beam 4. The seed beam 4 passes through a λ/2 plate 622 which arbitrarily changes the polarization surface, and is incident on a polarization beam splitter 621. A polarization surface of the seed beam 4 is inclined according to a rotation angle of the λ/2 plate. Here, the pump beam 3 is made to be a P polarization light. A P-polarization component of the seed beam 4 passes through a polarization beam splitter 621 and is incident on a terahertz wave generator 5, and an S-polarization component is branched into a reference seed beam 614. Even in a case where the polarization beam splitter 621 is installed at a position where the optical paths of the pump beam 3 and the seed beam 4 are close to each other, the pump beam 3 passes through the polarization beam splitter 621 because of the P polarization light. With this configuration, it is possible to be downsized. A branched reference seed beam 614 passes through the reference beam incident angle reversing optical system 32 and an angle thereof with respect to the optical axis is reversed and is incident on an interference optical system 11 at an angle θ. Further, a terahertz wave detection beam 9 is reversed in angle with respect to the optical axis by the detection light incident angle reversing optical system 31, and is incident on the interference optical system 11 at the angle θ.

Figure 11:
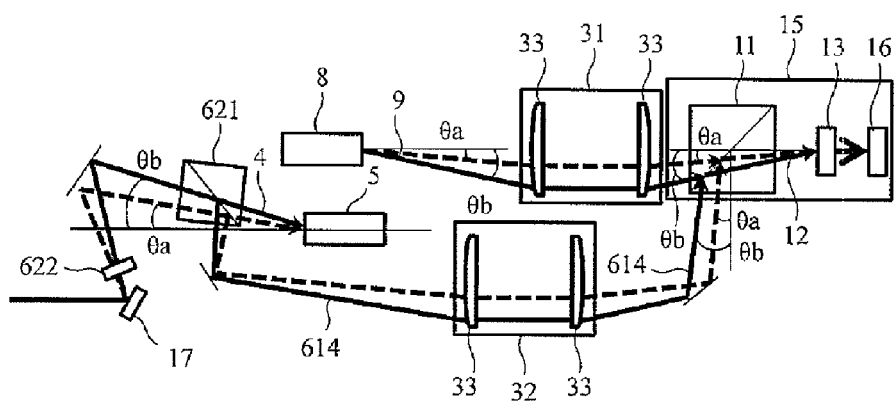
FIG. 11 is a diagram illustrating a change in the optical path in a case where the control angle θ is changed.

FIG. 11 is a diagram illustrating a change in the optical path in a case where the control angle θ is changed similar to the case of Example 3. In a case where the seed beam 4 is incident on the terahertz wave generator 5 by controlling the beam angle controller 17 so that the incident angle is at an angle θa at which the terahertz wave frequency becomes lower, the terahertz wave detection beam 9 follows the optical path indicated by a broken line, and is incident on the interference optical system 11 at an angle θa reversed with respect to the optical axis by a detection beam incident angle reversing optical system 31. On the other hand, the polarization is rotated by a λ/2 plate 622 to become an S polarization component, and a reference seed beam 614 branched by a polarization beam splitter 621 also follows the optical path indicated by a broken line, and is incident on the interference optical system 11 at the angle θa reversed with respect to the optical axis by a reference beam incident angle reversing optical system 32. The reference beam is reflected by a reflection surface of the beam splitter used in the interference optical system 11 and overlaps on the same optical path as the terahertz wave detection beam to generate the interference beam 12, the interference beam is incident on the photodetector 13, and the homodyne/phase diversity detection is performed.

Next, in a case where the seed beam 4 is incident on the terahertz wave generator 5 by controlling the beam angle controller 17 so that the incident angle is at an angle θb at which the terahertz wave frequency becomes higher, the terahertz wave detection beam 9 and the reference seed beam 614 travel on the optical paths respectively indicated by solid lines and are incident on the interference optical system 11. The terahertz wave detection beam 9 is incident on the interference optical system 11 at the angle θb reversed with respect to the optical axis by the detection beam incident angle reversing optical system 31. In addition, the reference seed beam 614 is incident on the interference optical system 11 at the angle θb reversed with respect to the optical axis by the reference beam incident angle reversing optical system 32. As a result, the terahertz wave detection beam 9 and the reference seed beam 614 travel on the same optical path and are incident on the interference optical system 11 to generate the interference beam 12, and the homodyne/phase diversity detection is performed.

As illustrated in the operation described above, the terahertz wave detection beam and the seed beam travel on the same optical path irrespective of the incident angle θ of the seed beam 4 on the terahertz wave generator 5 controlled by the beam angle controller 17, are incident on the interference optical system 11 to generate interference beam, and converge almost identically to the detection element of the photodetector. Therefore, all the incident angles are controlled by controlling only the beam angle controller 17, so that the terahertz wave detection beam and the reference beam can be multiplexed on the same optical path in the interference optical system 11 to interfere with each other. It is possible to perform the spectrum measurement by the homodyne/phase diversity detection. Therefore, it is possible to construct a compact and stable system.

Example 7

Figure 12:
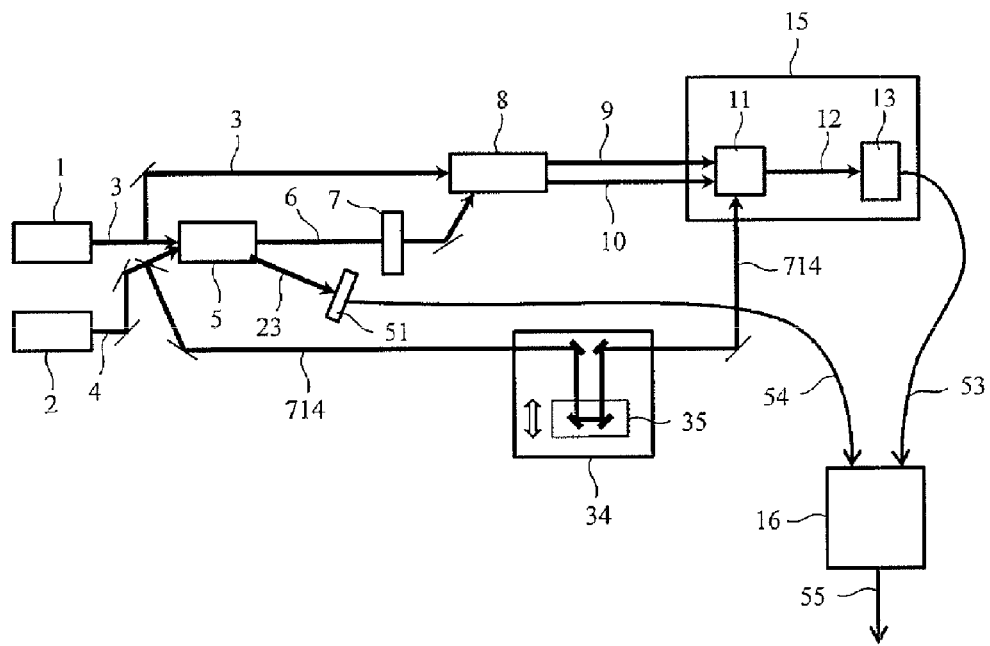
FIG. 12 is a block diagram illustrating an example of the terahertz wave measuring apparatus.

FIG. 12 is a block diagram illustrating a seventh example of a terahertz wave measuring apparatus of the invention. The example is an example in which some of the seed beam is branched and used as the reference beam.

In order to generate the interference beam, it is necessary to properly adjust the optical path length difference between the terahertz wave detection beam 9 and a reference seed beam 714, and to multiplex them within a pulse width range. For example, if the difference in the optical path length between the terahertz wave detection beam and the reference beam is expanded due to a difference in the dielectric constant of the measured object, a variation in the ambient temperature, a change due to transportation or aging of the optical system, or the like, there is a possibility that coherency deteriorates due to the difference in frequency and phase between the terahertz wave detection beam and the reference beam at a position at which both are multiplexed. Therefore, the reference seed beam 714 is incident on the variable optical delay line 34, and the reference seed beam 714 of which an optical path length is appropriately adjusted is incident on the interference optical system 11. As an example of the variable optical delay line 34, the optical delay device described in FIG. 7 can be used. In a case where the above-described external factors causing a large change in the optical path length occur, as described in Example 4, the operation illustrated in the flowchart of FIG. 8 is executed.

Furthermore, in order to stabilize the interference beam, a configuration is described in which a variation component caused by a light source or an optical amplifier which is a generation portion of the pump beam or the seed beam is extracted and is reduced from the interference beam. The idler beam 23 is detected by a photodetector 51 and a reference beam signal 54 is output to the signal processing unit 16. In addition, the interference beam signal 53 in which the interference beam 12 is detected by the photodetector 13 is output to the signal processing unit 16. An example of the calculation processing using the reference beam signal 54 is as described with reference to FIG. 9 in Example 4. In this way, the interference beam intensity signal from which the variation component is removed is output as a variation reducing interference beam signal 55.

Example 8

Figure 13:
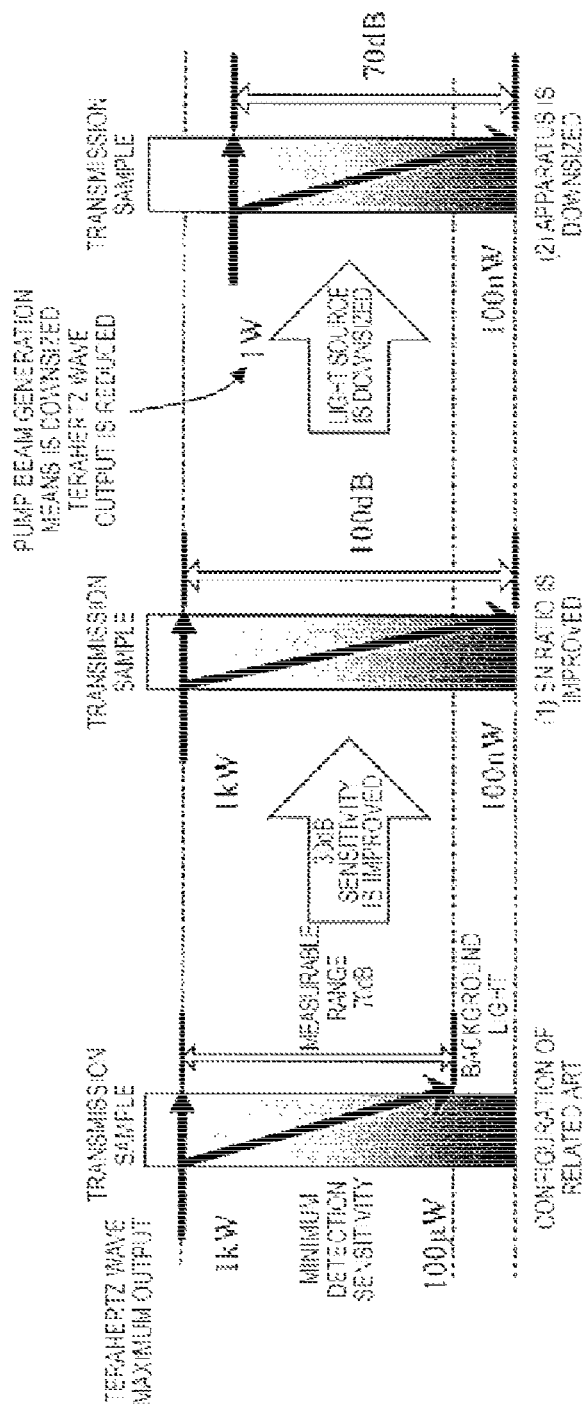
FIG. 13 is an explanatory view illustrating a measurable range of terahertz wave intensity.

FIG. 13 is an explanatory view illustrating a measurable range of a terahertz wave intensity. As illustrated in the level diagram of the configuration of the related art in FIG. 13, in a case where 100 μW of the background light is generated for a 1 kW tera wave output, the measurable range of the sample transmittance is 70 dB. It is possible to measure up to the minimum receiving sensitivity of the photodetector, and improve an SN ratio up to 100 dB by improving the sensitivity by substantially 30 dB by separating the background light. Furthermore, in a case where the SN ratio of 70 dB is maintained, the terahertz wave output can be reduced to 1 W, a necessary pump beam intensity can be alleviated and the light source can be downsized.

Figure 14:
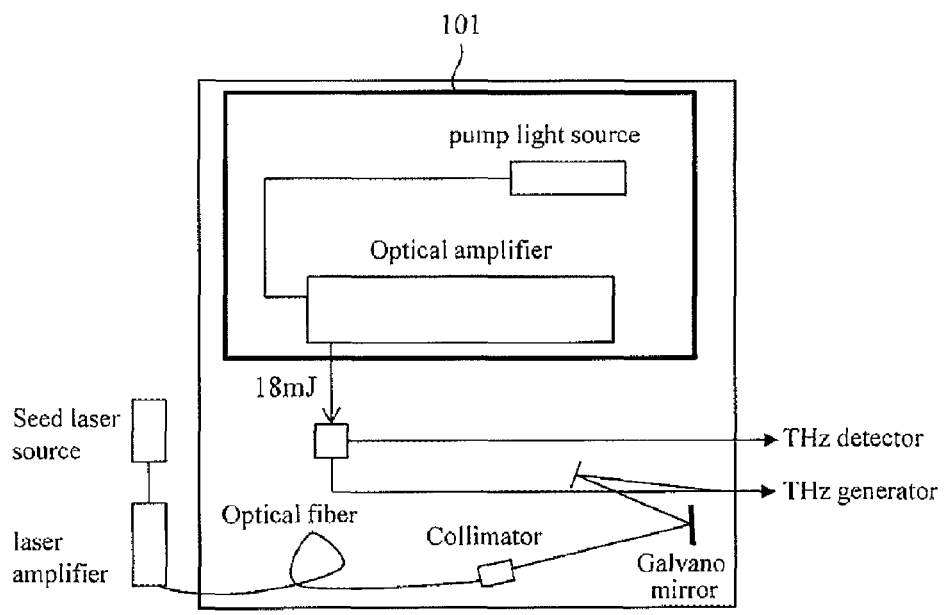
FIG. 14 is a schematic top view illustrating a configuration of a pump beam generator and a seed beam generator of the related art.
Figure 15:
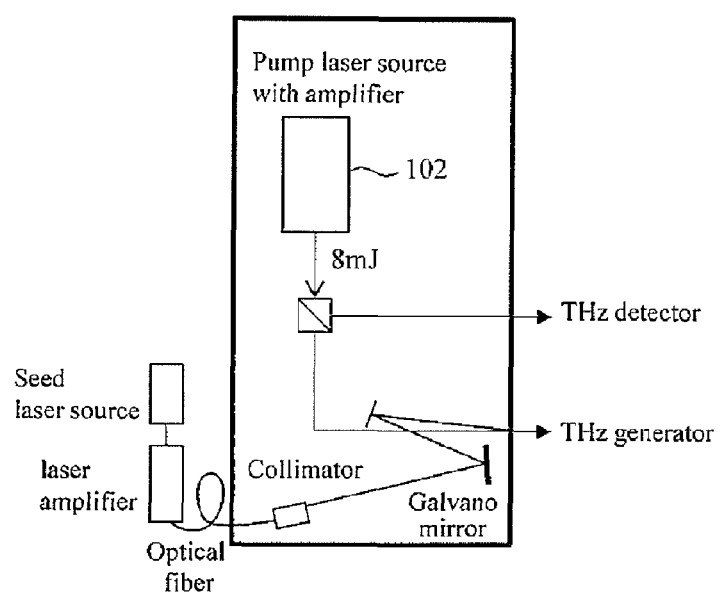
FIG. 15 is a schematic top view illustrating a configuration example of the pump beam generator and the seed beam generator which are downsized.

Here, a configuration example of the pump beam generator of the downsized terahertz wave measuring apparatus will be described. FIG. 14 is a schematic top view illustrating a configuration of a pump beam generator 101 and a seed beam generator of the related art. Since the pump beam generator 101 of the related art outputs substantially 18 mJ of the pump beam required to achieve a tera wave output of 1 kW, the pump beam source, an optical amplifier and a necessary optical path occupy an installation area. Considering the influence of the thermal lens effect, it is also necessary to secure the optical path length. Therefore, the occupied area is as large as about 0.5 m². On the other hand, FIG. 15 is a schematic top view illustrating a configuration example of a pump beam generator 102 and a seed beam generator which are downsized of the example. In the case of the terahertz wave output 1 W, the output of the pump beam can be reduced to 8 mJ and an amplifier can be built in the pump beam source. As a result, the installation area can be reduced to 0.25 m² which is substantially half of that of the related art. Further, as the optical path length is shortened and an operating temperature of the pump beam generator is decreased, the stability can be improved and the cost can be reduced.

Moreover, the invention is not limited to the above-described examples and various modifications are included. For example, the above-described examples are described in detail in order to explain the invention in an easy-to-understand manner, and are not necessarily limited to those having all the configurations described. Further, a part of the configurations of one example can be replaced with the configuration of another example, and the configuration of another example can be added to the configuration of one example. Further, it is possible to add, delete, and replace other configurations with respect to a part of the configuration of each example.

REFERENCE SIGNS LIST 1 pump beam generator
2 seed beam generator
3 pump beam
4 seed beam
5 terahertz wave generator
6 terahertz wave
7 measured object
8 terahertz wave detector
9 terahertz wave detection beam
10 background light
11 interference optical system
12 interference beam
13 photodetector
14 reference beam
15 homodyne/phase diversity detection optical system
16 signal processing unit
17 beam angle control unit
21 nonlinear optical crystal
22 silicon prism
23 idler beam
31 detection beam incident angle reversing optical system
32 reference beam incident angle reversing optical system
33 relay lens
34 variable optical delay line
35 variable optical line stage
51 photodetector
52 reference beam
53 interference beam signal
54 reference beam signal
55 variation reducing interference beam signal
514, 614, 714 reference seed beam
521 beam splitter
621 polarization beam splitter
622 λ/2 plate
811 space filter
341 polarization beam splitter
342 half beam splitter
343, 344 polarization beam splitter
381 differential circuit
382 differential circuit
401, 402 non-polarization beam splitter
403, 404, 405 polarizer
406, 407, 408 detector
408, 409, 410 phase plate
411 calculation circuit

The invention claimed is:

1. A terahertz wave measuring apparatus comprising:
a pulse laser light generator that generates a pump beam;
a seed beam generator that generates a seed beam;
a terahertz wave generator on which the pump beam and the seed beam are incident and which generates a terahertz wave;
a terahertz wave detector on which the terahertz wave generated from the terahertz wave generator and interacting with a measured object, and the pump beam are incident, and which generates a terahertz wave detection beam;
an interference optical system that multiplexes the terahertz wave detection beam and a reference beam having the same wavelength as that of the terahertz wave detection beam, and generates a plurality of interference beams having different phase relationships;
a plurality of photodetectors that detect the interference beam; and
a signal processing unit that calculates an output of the plurality of photodetectors and outputs an intensity signal and/or a phase signal of the terahertz wave interacting with the measured object,
wherein as the reference beam, a light obtained by being branched from an idler beam generated from the terahertz wave generator or a seed beam generated from the seed beam generator is used.

2. The terahertz wave measuring apparatus according to claim 1,
wherein the terahertz wave generator includes a first nonlinear optical crystal and the terahertz wave is generated by causing the pump beam and the seed beam which is angle-controlled to be incident on the first nonlinear optical crystal so as to satisfy a phase matching condition, and
wherein the terahertz wave detector includes a second nonlinear optical crystal, and the terahertz wave detection beam is generated by causing the terahertz wave and the pump beam which interact with the measured object to be incident on the second nonlinear optical crystal so as to satisfy the phase matching condition.

3. The terahertz wave measuring apparatus according to claim 1,
wherein the interference optical system generates four pieces of the interference beam,
wherein an interference phase of the terahertz wave detection beam and an interference phase of the reference beam are different from each other by an integer multiple of substantially 90 degrees, and
wherein a difference is obtained between outputs of two photodetectors that detect a pair of interference beams in which an interference phase of the terahertz wave detection beam and an interference phase of the reference beam are different from each other by substantially 180 degrees.

4. The terahertz wave measuring apparatus according to claim 1, wherein the idler beam generated from the terahertz wave generator is used as the reference beam.

5. The terahertz wave measuring apparatus according to claim 4, further comprising:
a beam angle controller that controls an incident angle of the seed beam on the terahertz wave generator; and
a first incident angle reversing optical system and a second incident angle reversing optical system which emit an incident light at an angle reversed with respect to an optical axis,
wherein the first incident angle reversing optical system is disposed in an optical path of the terahertz wave detection beam,
wherein the second incident angle reversing optical system is disposed in an optical path of the reference beam, and
wherein the terahertz wave detection beam and the reference beam are multiplexed on the same optical path in the interference optical system.

6. The terahertz wave measuring apparatus according to claim 4, further comprising an variable optical delay line,
wherein the terahertz wave detection beam and the idler beam passing through the variable optical delay line are multiplexed.

7. The terahertz wave measuring apparatus according to claim 4, further comprising a reference photodetector that detects some of the reference beam,
wherein the signal processing unit calculates a difference between a reference beam detection signal detected by the reference photodetector and a reference beam standard value acquired in advance as a variation value, and corrects an intensity signal of the terahertz wave interacting with the measured object using the variation value.

8. The terahertz wave measuring apparatus according to claim 1,
wherein as the reference beam, a light obtained by being branched from the seed beam generated from the seed beam generator is used.

9. The terahertz wave measuring apparatus according to claim 8, further comprising:
a beam angle controller that controls an incident angle of the seed beam on the terahertz wave generator; and
a first incident angle reversing optical system and a second incident angle reversing optical system which emit an incident light at an angle reversed with respect to the optical axis,
wherein the first incident angle reversing optical system is disposed in the optical path of the terahertz wave detection beam,
wherein the second incident angle reversing optical system is disposed in the optical path of the reference beam, and
wherein the terahertz wave detection beam and the reference beam are multiplexed on the same optical path in the interference optical system.

10. The terahertz wave measuring apparatus according to claim 9,
wherein a wavelength plate and a polarization beam splitter are disposed in an incident optical path of the seed beam on the terahertz wave generator,
wherein the seed beam which is angle-controlled by the beam angle controller passes through the wavelength plate and is incident on the polarization beam splitter so that an angle formed by the pump beam and a polarization surface becomes a predetermined angle, and
wherein the seed beam branched by the polarization beam splitter is incident on the interference optical system as the reference beam.

11. The terahertz wave measuring apparatus according to claim 8, further comprising an variable optical delay line,
wherein the terahertz wave detection beam and the reference beam passing through the variable optical delay line are multiplexed.

\* \* \* \* \*